US006562971B2

(12) United States Patent
Frauenkron et al.

(10) Patent No.: US 6,562,971 B2
(45) Date of Patent: May 13, 2003

(54) PROCESS FOR THE PREPARATION OF TRIETHYLENEDIAMINE (TEDA)

(75) Inventors: Matthias Frauenkron, Ludwigshafen (DE); Bernd Stein, Seeheim-Jugenheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/765,625

(22) Filed: Jun. 26, 2001

(65) Prior Publication Data

US 2002/0107394 A1 Aug. 8, 2002

(30) Foreign Application Priority Data

Dec. 12, 2000 (DE) .......................... 100 61 863

(51) Int. Cl.[7] ................... C07D 295/023; C07D 487/08
(52) U.S. Cl. ...................................... 544/352
(58) Field of Search ........................ 544/352

(56) References Cited

U.S. PATENT DOCUMENTS

| | | | | |
|---|---|---|---|---|
| 2,937,176 A | | 5/1960 | Herrick ................. | 260/268 |
| 3,285,920 A | | 11/1966 | Muhlbauer et al. ......... | 260/268 |
| 3,702,886 A | | 11/1972 | Argauer et al. ........... | 423/328 |
| 3,956,329 A | | 5/1976 | Murakami et al. ......... | 260/268 |
| 4,289,881 A | | 9/1981 | Imre et al. ................. | 544/352 |
| 4,804,758 A | | 2/1989 | Hoelderich et al. ........ | 544/352 |
| 4,966,969 A | | 10/1990 | Sato et al. ................ | 544/352 |
| 5,041,548 A | * | 8/1991 | Sato et al. ................ | 544/116 |
| 5,280,120 A | * | 1/1994 | King ........................ | 544/352 |
| 5,731,449 A | | 3/1998 | Li et al. ................... | 544/352 |
| 5,741,906 A | | 4/1998 | Santieteban et al. ....... | 544/352 |
| 5,756,741 A | | 5/1998 | Armor et al. .............. | 544/352 |
| 6,084,096 A | * | 7/2000 | Li et al. ................... | 544/352 |
| 6,350,874 B1 | * | 2/2002 | Ogawa ..................... | 544/352 |
| 6,380,119 B1 | | 4/2002 | Grosch et al. ............. | 502/49 |

FOREIGN PATENT DOCUMENTS

| | | |
|---|---|---|
| DE | 206 896 | 2/1984 |
| EP | 158 319 | 10/1985 |
| EP | 312 734 | 4/1989 |
| EP | 313 753 | 5/1989 |
| EP | 349 859 | 1/1990 |
| EP | 382 055 | 8/1990 |
| EP | 423 526 | 4/1991 |
| EP | 831 096 | 3/1998 |
| EP | 1 041 073 | 10/2000 |
| RU | 2071475 | 1/1997 |
| RU | 2114849 | 7/1998 |
| WO | WO 89/05810 | 6/1989 |
| WO | WO 01/02404 | 1/2001 |

OTHER PUBLICATIONS

Reichle, W.T., J. Catalysis, 144, 1993, 556–568.*
Weitkamp et al., *Catalysis and Zeolites, Fundamentals and Applications*, Chapter 3 pp. 81–197, 1999.
Ullmann's, Encyclopedia of Industrial Chemistry, 5th Ed., vol. A28, pp. 487 to490 on "Zeo–lites" (VCH Publishers, 1996).
Klockemann et al, "Method for the production of triethylene diamine making use of ethylene dia–mine"; U.S. patent application Ser. No. 09/609,740.
Reichle "Reactions of Aliphatic α–ω–Diamines in H[+]–Pentasils" Journal of Catalysts vol. 144 (1993) pp. 556–568.

* cited by examiner

Primary Examiner—Mukund J. Shah
Assistant Examiner—Thomas McKenzie
(74) Attorney, Agent, or Firm—Keil & Weinkauf

(57) ABSTRACT

A process for the preparation of triethylenediamine (TEDA) by reaction of ethylenediamine (EDA) in the presence of a zeolite catalyst, wherein the zeolite catalyst comprises one or more metals M in oxidation states II, III or IV as oxides, and for M=Al, has an $SiO_2/M_2O_3$ molar ratio of greater than 1400:1, for M=metal in oxidation state II or M=two or more metals in oxidation state II, has an $SiO_2/MO$ molar ratio of greater than 100:1, for M=metal in oxidation state III or M=two or more metals in oxidation state III, has an $SiO_2/M_2O_3$ molar ratio of greater than 100:1 and for M=metal in oxidation state IV or M=two or more metals in oxidation state IV, has an $SiO_2/MO_2$ molar ratio of greater than 10:1, and the reaction temperature is from 250 to 500° C.

31 Claims, No Drawings

PROCESS FOR THE PREPARATION OF TRIETHYLENEDIAMINE (TEDA)

The present invention relates to a process for the preparation of triethylenediamine (TEDA) by reaction of ethylenediamine (EDA) in the presence of a zeolite catalyst.

Triethylenediamine (TEDA=DABCO®=1,4-diazabicyclo[2.2.2]octane) is an important basic chemical and is used, inter alia, in the preparation of pharmaceuticals and plastics, in particular as catalyst in the preparation of polyurethanes.

The known processes for the preparation of TEDA essentially differ through the nature of the starting materials and the catalysts. It is basically advantageous for the starting materials employed to be favorable basic chemicals, for example monoethanolamine (MEOA) or ethylenediamine (1,2-diaminoethane, EDA). However, conventional processes have proven to have very low selectivity, in particular with respect to the starting material EDA. In addition, the removal of the impurities which form during the cyclization reaction is difficult, and consequently these processes have not been able to establish themselves in industry.

The process described in U.S. Pat. No. 3,285,920 (H.G. Muhlbauer et al., Jefferson Chemical Co.) for the simultaneous preparation of TEDA and piperazine (referred to as PIP below) is a two-step process in which firstly EDA, ethanolamine and/or oligomers thereof are reacted in the presence of ammonia and hydrogen to give a mixture of piperazine and N-(beta-aminoethyl)piperazine in a reductive amination process using metal-oxide hydrogenation catalysts, and the remainder after removal of the piperazine is cyclized in the presence of cyclization catalysts, such as phosphate salts and aluminosilicates. The yields of TEDA are about 25% and those of PIP are about 12%.

U.S. Pat. No. 2,937,176 (Houdry Process Corp.) relates to the preparation of TEDA by gas-phase reaction of an alkylenepolyamine or alkanolamine in the presence of a solid acidic catalyst, such as silica-alumina, at temperatures of from 300 to 500° C. The TEDA is purified by crystallization from hydrocarbons, preferably pentane.

DE-A-24 34 913 (Shunan Petrochemicals) (equivalent: U.S. Pat. No. 3,956,329) describes the use of pentasil zeolites for the synthesis of TEDA from amines, such as N-aminoethylpiperazine,
PIP or EDA, by reaction on zeolites of types A, X and Y of the general formula $a(M_{2/n}O) (Al_2O_3) m(SiO_2)$, where M=an alkali metal, alkaline-earth metal, an element from the zinc group, $H^+$ or $NH_4{}^+$; n=valency of the cation; a=1.0+0.5; n=2–12. For conversion into the desired form, the zeolites are treated with an aqueous solution of hydrochloric acid for ion exchange with hydrogen cations or with metal halides for ion exchange with the desired metal cations.

EP-A-158 319 (Union Carbide Corp.) relates to the preparation of 1-azabicyclo[2.2.2]octane and 1,4-diazabicyclo[2.2.2]octanes from acyclic or heterocyclic amines in the presence of a 'high-silica zeolite' catalyst.

EP-A-313 753 (equivalent: DE-A1-37 35 212) and EP-A-312 734 (equivalent: DE-A1-37 35 214) (both Hüls AG) disclose a process for the preparation of a PIP/TEDA mixture by reaction of ethanolamines and/or ethylenediamine in the presence of a zeolite of the pentasil type. In accordance with the process, the reaction mixture is passed in gaseous form over a fixed-bed catalyst at from 280 to 380° C., and LHSV (liquid hourly space velocity) of from 0.1 to $10h^{-1}$ and at an absolute pressure of from 0.1 to 10 bar. It is also proposed that the starting compounds be employed together with a diluent, for example water. Maximum TEDA selectivities of 46% are achieved.

According to EP-A-382 055 (equivalent: DE-A-39 03 622, BASF AG), 1,2-diaminoethane (EDA) and from 0 to 200 mol % of piperazine are converted into TEDA on aluminum, boron, gallium and/or iron silicate zeolites under the following preferred reaction conditions, in the case of a liquid-phase reaction: reaction temperature from 100 to 300° C., pressure from 1 to 5 bar and WHSV from 1 to $10h^{-1}$. The reaction is preferably carried out in the gas phase at a reaction temperature of from 200 to 400° C., a pressure of from 0.5 to 5 bar and an WHSV of from 1 to $10h^{-1}$. A solvent or diluent, such as water, may be added. In the preferred gas-phase procedure, yields of TEDA of up to 70% are obtained. As a particular preparation procedures, treatment with aqueous hydrochloric acid after the shaping of the zeolites, and subsequent calcination at from 400 to 500° C. is described.

EP-A-423 526 (equivalent: DE-A-39 34 459, Bayer AG) describes a process for the preparation of TEDA and PIP by reaction of EDA on zeolites of the pentasil type with reduced acidity. According to the this application, zeolites of this type are obtainable by exchange of at least 50% of all exchangeable cations by alkali metal cations or are those in which the aluminum of the zeolite structure is replaced isomorphically by iron. According to this application, ZSM-5 catalysts which have not been treated by this process have proven to be less suitable. The reaction is carried out at a temperature of from 300 to 400° C. and at a weight hourly space velocity of from 0.03 to 2.0 kg (EDA)/kg (zeolite)/h, using EDA/water mixtures comprising from 2 to 25 mol, preferably from 5 to 15 mol, of water per mole of EDA. Selectivities with respect to TEDA of up to 65% are achieved.

U.S. Pat. No. 4,966,969 (Idemitsu Kosan) describes a method for the preparation of TEDA from amine-containing compounds, for example monoethanolamine, ethylenediamine, piperazine or piperazine derivatives, on metal silicates of the pentasil type which have $SiO_2/Al_2O_3$ ratios of greater than 12 and which have been calcined at 400–600° C. under air, at reaction temperatures of 100–500° C. and pressures from 3 bar.

U.S. Pat. No. 5,041,548 (Idemitsu Kosan Ltd) proposes, inter alia, using pentasil zeolites ($SiO_2/M_{2\ O3}$: for example H-ZSM5, $SiO_2/Al_2O_3$=45–90) prepared in the presence of organic templates, such as tetraalkylammonium compounds, in the reaction of amine-containing compounds, for example monoethanolamine, ethylenediamine or piperazine, for the preparation of TEDA. In the reaction of EDA/water mixtures at 400° C., TEDA yields of 45% are achieved. Pentasil zeolites prepared without an organic template exhibit significantly worse TEDA yields in the reactions of the amine-containing compounds at 350–400° C.

EP-A-831 096, EP-A-842 936 and EP-A-952 152 (Air Products and Chemicals Inc.) describe processes for the preparation of TEDA from EDA or monoethanolamine using specially modified pentasil zeolites:

According to EP-A-831 096 (equivalent: U.S. Pat. No. 5,731,449), caustic lye treatment of a pentasil zeolite (Na-ZSM5, $SiO_2/Al_2O_3$=160) which has subsequently been converted into the $H^+$ form by means of $NH_4NO_3$ solution and calcination (H-ZSM5, $SiO_2/Al_{2\ O3}$=153) enables an increase in the selectivity with respect to TEDA from 23% to 56% and in the long-term stability to 32 hours to be achieved without visible deactivation in the reaction of an EDA/water mixture at 340° C. compared with untreated zeolites. The effect is explained by passivation of the active centers (hydroxyl groups, analysis by IR spectroscopy) on the external, outer surface of the zeolite as a consequence of the caustic-lye treatments.

According to EP-A-842 936 (equivalent: U.S. Pat. No. 5,741,906), pretreatment with a dealuminating agent (chelating agent for removal of aluminum, for example oxalic acid) likewise enables the external, outer surface of pentasil zeolites (H-ZSM5, $SiO_2/Al_2O_3$=180) to be passivated and thus, for example, improved selectivity to be achieved in the synthesis of TEDA from monoethanolamine, piperazine and water at 350° C. of up to 30% compared with untreated zeolites.

According to EP-A-952 152 (equivalent: U.S. Pat. No. 6,084,096), surface passivation of the pentasil zeolites can likewise be achieved by treatment with a silicon compound followed by calcination. The treatment of a very finely crystalline pentasil zeolite (H-ZSM5, $SiO_2/Al_2O_3$=90, crystal size: 0.07 μm) with a solution of tetraethoxysilane in ethanol followed by calcination enabled, for example, the selectivity with respect to TEDA and PIP in the reaction of an EDA/water mixture at 340° C. to be increased from 81% to 89% compared with the untreated material with a slight drop in activity.

EP-A-842 935 (equivalent: U.S. Pat. No. 5,756,741) (Air Products and Chemicals Inc.) describes a two-step process in which firstly a piperazine-rich intermediate is prepared from an amino compound by a cyclization reaction, and this intermediate is then converted into TEDA with addition of, for example, EDA on a pentasil zeolite. It is claimed that this special two-step procedure minimizes or even eliminates the necessity for PIP recycling in the synthesis of TEDA.

EP-A-1 041 073 (Tosoh Corp.) relates to a process for the preparation of triethylenediamines and piperazines by bringing certain compounds containing an aminoethyl group into contact with a crystalline aluminosilicate in which the silica/alumina ratio is at least 12. The shaped aluminosilicate is calcined at a temperature of 500–950° C., preferably at 550–850° C., for at least one (preferably 3) hours. The calcination is followed by acid treatment with an aqueous inorganic acid at 50–80° C. for from 3 to 50 hours.

U.S. Pat. No. 4,289,881 (Bayer AG; equivalent: EP-A-10 671) describes the preparation of TEDA from certain piperazine derivatives in the presence of an $SiO_2$ catalyst.

DD-A-206 896 (VEB Leuna-Werke) relates to a process for the preparation of TEDA by reaction of N-(beta-aminoethyl)piperazine and/or N-(beta-hydroxyethyl)piperazine on a porous $SiO_2/Al_2O_3$ catalyst in the presence of $NH_3$.

Derwent Abstract No. 1997-371381 (RU-A-20 71 475 (AS Sibe Catalysis Inst.)) describes the preparation of triethylenediamines from monoethanolamine on a pentasil zeolite which has been treated with an aqueous solution of a complexing agent.

RU-C1-21 14 849 (Institute for Technology and Construction of Catalysis and Adsorption Processes using "Tseosite" Zeolite SO RAN) (Derwent Abstract No. 2000-036595) describes processes for the preparation of TEDA from a mixture of monoethanolamine (MEOA), EDA and PIP on pentasil zeolites having a modulus ($SiO_2/Al_2O_3$ molar ratio) of 40–300. The zeolites used are dealuminated by treatment with an aluminum chelating agent (EDTA, sulfosalicylic acid, TMAOH). The patent specifically describes the reaction of MEOA/EDA, MEOA/PIP, EDA/PIP and EDA/MEOA/PIP mixtures with $NH_3$ or water as diluent (1:3-10) on correspondingly treated zeolites at 350–450° C. The reactor product is separated into boiling ranges by rectification. The range 160–180° C. is subsequently cooled and crystallized out. The mother liquor is re-employed as starting material.

A common feature of the prior-art processes is the low selectivity with respect to the formation of TEDA, a very high and thus possibly uneconomical proportion of water as diluent or solvent in the reactor feed, an inadequate catalyst service life, for example as a consequence of deactivation, and possibly in addition complex catalyst preparation and/or modification.

It is an object of the present invention to find an economical process for the preparation of TEDA from readily accessible starting compounds which is improved compared with the prior art, is simple to carry out, has high yield, selectivity and catalyst service life and low unavoidable formation of piperazine and which gives the TEDA in high purity, color stability (i.e. low color number in accordance with ISO 6271, which also remains small over extended storage times, for example 6, 12 or more months, and odor quality [i.e. is possible only as an inherent odor of TEDA and no odor of cyclic saturated N-heterocyclic compounds with 5-membered rings or other cyclic saturated N-heterocyclic compounds with 6-membered rings (for example PIP or N-ethylpiperazine) and/or aromatic N-heterocyclic compounds with 5- or 6-membered rings].

We have found that this object is achieved by a process for the preparation of triethylenediamine (TEDA) by reaction of ethylenediamine (EDA) in the presence of a zeolite catalyst, wherein the zeolite catalyst comprises one or more metals M in oxidation state II, III or IV as oxides, and for M=Al, has an $SiO_2/M_2O_3$ molar ratio of greater than 1400:1, for M=metal in oxidation state II or M=two or more metals in oxidation state II, has an $SiO_2$/MO molar ratio of greater than 100:1, for M=metal in oxidation state III or M=two or more metals in oxidation state III, has an $SiO_2/M_2O_3$ molar ratio of greater than 100:1, and for M=metal in oxidation state IV or M=two or more metals in oxidation state IV, has an $SiO_2/MO_2$ molar ratio of greater than 10:1, and the reaction temperature is from 250 to 500° C.

The process according to the invention can be carried out batchwise or preferably continuously.

The reaction according to the invention can be carried out in the liquid phase or preferably in the gas phase.

The reaction is preferably carried out in the presence of a solvent or diluent.

Examples of suitable solvents or diluents are acyclic or cyclic ethers having 2 to 12 carbon atoms, such as dimethyl ether, diethyl ether, di-n-propyl ether or isomers thereof, MTBE, THF, pyran, or lactones, such as gamma-butyrolactone, polyethers, such as monoglyme, diglyme, etc., aromatic or aliphatic hydrocarbons, such as benzene, toluene, xylene, pentane, cyclopentane, hexane and petroleum ether, or mixtures thereof and particularly also N-methylpyrrolidone (NMP) or water or aqueous organic solvents or diluents of the abovementioned type. Ammonia is also a suitable solvent or diluent.

The particularly preferred solvent or diluent, in particularly solvent, is water.

Suitable diluents when carrying out the reaction in the gas phase are also inert gases, such as nitrogen (for example beyond the saturation of the reactor feed) or argon. The reaction in the gas phase is preferably carried out in the presence of ammonia.

For example, the reaction is carried out in the presence of from 2 to 1200% by weight, particularly from 12 to 1200% by weight, in particular from 14 to 300% by weight, very particularly from 23 to 300% by weight, of solvents or diluents, based on EDA employed.

For example, the starting mixture employed in the process or the reactor feed (=starting material stream in the case of the continuous procedure) comprises from 5 to 80% by weight, particularly from 10 to 80% by weight, particularly preferably from 20 to 70% by weight, very particularly preferably from 20 to 65% by weight, of EDA and from 2 to 60% by weight, particularly from 10 to 60% by weight, particularly preferably from 15 to 60% 15 by weight, in particular from 20 to 50% by weight, of the solvent(s) and diluent(s).

In a particular embodiment of the process according to the invention, EDA and one or more amine compounds each containing a 2-aminoethyl group, —HN—CH$_2$—CH$_2$—, are reacted.

Amine compounds of this type are preferably ethanolamines (for example monoethanolamine (MEOA), diethanolamine (DEOA) or triethanolamine (TEOA)), piperazine (PIP), diethylenetriamine (DETA), triethylenetetramine (TETA), tri(2-aminoethyl)amine, N-(2-aminoethyl) ethanolamine (AEEA) and piperazine derivatives, for example N-(2-hydroxyethyl)piperazine (HEP) and N-(2-aminoethyl)piperazine (AEPIP).

PIP is particularly preferred.

The content of these amine compounds in the reactor feed is in this particular embodiment (in total) generally from 1 to 1000% by weight, preferably from 3 to 250% by weight, in particular from 7 to 250% by weight, in each case based on EDA employed.

For example, the starting mixture employed in the process or the reactor feed (=starting-material stream in the case of the continuous procedure) comprises (in total) from 0.5 to 50% by weight, preferably from 2 to 50% by weight, in particular from 5 to 50% by weight, of these amine compounds.

Since it has also been found that in this particular embodiment the formation of by products which can only be removed from the reactor product (=product stream in the case of the continuous procedure) with difficulty can occur in the starting mixture or in the reactor feed if MEOA is employed, the content of this amine compound in the starting mixture or reactor feed is preferably from 1 to 50% by weight, based on EDA employed.

After the reaction, the products formed are isolated from the reaction product mixture by conventional methods, for example by distillation and/or rectification; unreacted starting materials can be fed back into the reaction.

Thus, PIP arising in the reaction product mixture from the process according to the invention can be removed therefrom, for example by distillation, and fed back into the reaction.

A particular advantage of the process is that intermediate fractions containing both TEDA and piperazine which are obtained on work-up of the reaction product mixture, and fractions which contain, for example, N-(2-hydroxyethyl) piperazine (HEP), N-(2-aminoethyl)piperazine (AEPIP), diethylenetriamine (DETA), triethylenetetramine (TETA), tri(2-aminoethyl)amine and/or N-(2-aminoethyl) ethanolamine (AEEA) can be fed back into the reaction again.

Furthermore, unavoidable formation of other amine compounds from other amine cyclization/condensation reactions can be fed to the reaction according to the invention without the yields of TEDA being significantly impaired.

In a particularly preferred embodiment, the process according to the invention is carried out, in particular in the case of the continuous procedure (steady state), by reacting EDA and from 14 to 300% by weight of water and from 7 to 250% by weight of PIP, in each case based on EDA, preferably EDA and from 23 to 300% by water and from 8 to 250% by weight of PIP, in each case based on EDA, particularly preferably EDA and from 33 to 250% by weight of water and from 17 to 250% by weight of PIP, in each case based on EDA, very particularly preferably EDA and from 110 to 185% by weight of water and from 25 to 100% by weight of PIP, in each case based on EDA.

In this embodiment, the proportion of the PIP or EDA can also be reduced or increased to the extent of from 0.01 to 20% by weight, for example from 0.01 to 10% by weight, in favor of one and at the expense of the other.

For example, the starting mixture employed in the process or the reactor feed comprises in this particularly preferred embodiment from 10 to 60% by weight of water, from 20 to 70% by weight of EDA and from 5 to 50% by weight of PIP, preferably from 15 to 60% by weight of water, from 20 to 65% by weight of EDA and from 5 to 50% by weight of PIP, particularly preferably from 20 to 50% by weight of water, from 20 to 60% by weight of EDA and from 10 to 50% by weight of PIP, very particularly preferably from 45 to 55% by weight of water, from 30 to 40% by weight of EDA and from 10 to 30% by weight of PIP, where the proportion of the PIP or EDA can also be reduced or increased to the extent as described above in favor of one and at the expense of the other.

In this particularly preferred embodiment of the process, the reactor feed, in addition to EDA, PIP and water in the above-stated mixing ratios or amounts, preferably comprises less than 10% by weight, particularly less than 5% by weight, in particular less than 2% by weight, of further components.

In this particularly preferred embodiment, it has been found that at the above-stated mixing ratios or amounts of the starting materials, the reaction, in particular in the case of the continuous procedure (in the steady state) can be carried out in such a way that EDA is converted virtually completely (i.e. conversion greater than 95%, in particular greater than 97%) into TEDA and PIP with a selectivity of greater than 90%, in particular greater than 95%.

The process is preferably carried out in accordance with the invention by setting an appropriate EDA/PIP ratio in the reactor feed (=starting-material stream in the case of the continuous procedure) in the abovementioned ranges so that the consumption of PIP in the overall balance approaches zero (for example from 0 to 30 kg, in particular from 0 to 15 kg, very particularly from 0 to 10 kg, per 100 kg of TEDA in the reaction product mixture), in particular is zero, through removal of PIP from the reaction product mixture and recycling into the reactor feed, and at the same time the EDA employed is reacted completely (>95%, in particular >97%, very particularly >99%), i.e. as a result essentially no additional PIP is fed to the process according to the invention during the continuous procedure.

Since, if the reaction is carried out in this way, the amount of discharged EDA approaches zero in accordance with the invention, the separation of the reactor product mixture, for example by distillation and/or rectification, is particularly simple in this process variant.

The reaction temperature in the process according to the invention is preferably from 300 to 400° C., particularly preferably from 310 to 390° C.

The starting-material components or the reactor feed are advantageously brought to temperature in advance.

For carrying out the process according to the invention, the following reaction conditions have furthermore proven favorable:

- a WHSV (weight hourly space velocity), based on the amines employed in the reaction, of from 0.05 to $6h^{-1}$, preferably from 0.1 to 1 $h^{-1}$, particularly preferably from 0.3 to 1 $h^{-1}$, and
- a pressure (absolute) of from 0.01 to 40 bar, particularly from 0.1 to 10 bar, preferably from 0.8 to 2 bar.

Suitable reactors in which the process according to the invention is carried out are stirred-tank reactors, in particular tubular reactors and tube-bundle reactors.

The zeolite catalyst is preferably arranged in the reactor in the form of a fixed bed.

The reaction in the liquid phase can be carried out, for example, by the suspension, trickle or pool method.

The preferred reaction in the gas phase can be carried out in a fluidized bed or preferably fixed bed of catalyst.

The following paragraph additionally outlines by way of example how the process according to the invention can be carried out:

The reactor feed (composition as described above) is converted into the gas phase in an evaporator, which may, if desired, be part of the actual reactor, at a temperature of 250–500° C. and fed onto the catalyst. The reaction product mixture arising in gas form at the reactor outlet is quenched at temperatures of 20–100° C., preferably at 80° C., by liquefied reaction product mixture circulated by pumping. This liquefied reaction product mixture is worked up as follows: in a first distillation step, low-boiling components, such as acetaldehyde, ethylamine, ammonia and water, and heterocyclic compounds formed as by-products in the synthesis are separated off. In a second distillation step, the reaction product mixture is freed from piperazine, which is fed back to the reactor feed. The stream of separated-off piperazine here may comprise up to 20% by weight of TEDA. (Alternatively, it is also possible to remove water and piperazine simultaneously, which can be fed back together into the reactor feed). In a preferred distillation step, the target product TEDA is recovered from the reaction product mixture by distillation and, if necessary, worked up further, for example in a subsequent crystallization step (for example as described below).

The following advantages, inter alia, are achieved with the process according to the invention:

- The process allows the EDA employed as starting material to be replaced, depending on price and availability, by one or more amine compounds each having a 2-aminoethyl group, —HN—CH$_2$—CH$_2$—, (see above), or these amine compounds additionally to be added to the reactor feed.
- Piperazine, essentially the only by-product, can, if the reaction is carried out in a suitable manner as described above, be fed back into the process and converted into TEDA. Mixtures of unreacted piperazine and TEDA can also be fed back to the catalyst, since it has been found that TEDA is stable under the reaction conditions.
- Given a suitable choice of the EDA/PIP ratio in the reactor feed as described above, the consumption of PIP in the overall balance approaches zero, since on recycling of the PIP present in the reaction product mixture, a constant PIP stream in terms of volume is obtained in the reactor feed and thus exclusively EDA as the only amine in the overall balance must be fed continuously to the reaction from the outside.
- High selectivity and high conversion, based on the reaction of EDA to give TEDA, are achieved.
- Owing to the zeolite catalysts used in accordance with the invention, fewer by-products are formed in the reaction of EDA and, if used, the abovementioned amine compounds, which results in simplified work-up of the TEDA formed in the process in order to achieve the requisite product specifications (purity, color number and odor).

The zeolite employed as catalyst in the process according to the invention for the preparation of TEDA has a skeletal structure which principally consists of silicon dioxide ($SiO_2$).

Besides silicon dioxide, the zeolite may also contain traces of other divalent, trivalent or tetravalent metals M (oxidation state of the metals II, III or IV) in the form of metal oxides $M_{2/z}O$ (z=2, 3 or 4), where the molar ratio of silicon dioxide and the metal oxide, $SiO_2/M_{2/z}O$ (this molar ratio is also known as the 'modulus') is greater than 10 for tetravalent metals (z=4), greater than 100 for divalent and trivalent metals (z=2 or 3) and greater than 1400 for M=Al (z=3).

The zeolite catalysts preferably used in the process according to the invention have, for M=Al, an $SiO_2/M_2O_3$ molar ratio of from greater than 1400 to 40,000:1, in particular from greater than 1400 to 5000:1,

- for M=metal in oxidation state II or M=two or more metals in oxidation state II, have an $SiO_2/MO$ molar ratio of from greater than 100 to 40,000:1, in particular from greater than 200 to 5000:1,
- for M=metal in oxidation state III or M=two or more metals in oxidation state III, have an $SiO_2/M_2O_3$ molar ratio of from greater than 100 to 40,000:1, in particular from greater than 200 to 5000:1, and
- for M=metal in oxidation state IV or M=two or more metals in oxidation state IV, have an $SiO_2/MO_2$ molar ratio of from greater than 10 to 40,000:1, in particular from greater than 25 to 5000:1.

The zeolite catalyst used in the process according to the invention is preferably of the pentasil type.

The upper limit of the modulus (40,000) is set only by the purity of the starting substances (residual traces of M or compounds of M) and the purity and chemical resistance of the apparatuses employed in the synthesis of the zeolite.

For a modulus below the stated limit, the Brönsted and Lewis acidity density (acidity density: acid centers/total catalyst surface area) of the zeolites increases significantly, the achievable TEDA yield and selectivity and the catalyst service life drop significantly, and the cost of purifying the TEDA increases significantly.

Surprisingly, it has been found that the drastic reduction in the acidity within the zeolite crystal in the process according to the invention due to the incorporation of divalent and/or trivalent metals in the form of metal oxides (M for z=2 or 3) in the lattice in the normal case during the hydrothermal synthesis results in the advantages according to the invention, for example a significant improvement in the selectivity with respect to TEDA. Zeolites containing tetravalent metals in the form of metal oxides (M for z=4) in the zeolite lattice also achieve improved selectivity with respect to TEDA in accordance with the invention.

For the zeolite catalyst, preferably of the pentasil type, having moduli as indicated above, there are neither additional requirements with respect to the zeolite material as such nor with respect to the process by which this is obtainable.

In the zeolite catalyst used in the process according to the invention, which, besides $SiO_2$, also contains one or more metals M in oxidation states II, III or IV as oxides, the metal M in oxidation state II is preferably selected from the group consisting of Zn, Sn and Be, and mixtures thereof, the metal M in oxidation state III is preferably selected from the group consisting of Al, B, Fe, Co, Ni, V, Mo, Mn, As, Sb, Bi, La, Ga, In, Y, Sc and Cr, and mixtures thereof, and the metal M in oxidation state IV is preferably selected from the group consisting of Ti, Zr, Ge, Hf and Sn, and mixtures thereof.

reference is given to zeolites in which M is aluminum, gallium, titanium, zirconium, germanium, iron or boron. Those in which M is aluminum, titanium, iron or boron are particularly preferred.

Examples of suitable zeolite catalysts of the pentasil type which are to be employed in accordance with the invention are the following types: ZSM-5 (as disclosed in U.S. Pat. No. 3,702,886), ZSM-11 (as disclosed in U.S. Pat. No. 3,709,979), ZSM-23, ZSM-53, NU-87, ZSM-35, ZSM-48 and mixed structures comprising at least two of the above-mentioned zeolites, in particular ZSM-5 and ZSM-11, and mixed structures thereof.

Particular preference is given for the process according to the invention to zeolites having an MFI or MEL structure or an MEL/MFI or MFI/MEL mixed structure.

The zeolites used in according with the invention are crystalline metal silicates having an ordered channel and cage structure with micropores. The network of such zeolites is built up from $SiO_4$ and $M_{2/z}O$ (z=2, 3 or 4) tetrahedra which are bonded via joint oxygen bridges. A review of the known structures is given, for example, in W. M. Meier, D. H. Olsen and Ch. Baerlocher in "Atlas of Zeolite Structure Types", Elsevier, $4^{th}$ Edition, London 1996.

Also suitable in accordance with the invention are zeolites which contain no aluminum (M=Al) and in which the Si(IV) in the zeolite lattice has been partially replaced by a metal M(IV), for example Ti, Zr, Ge, Hf and/or Sn, partially by a metal M(II), for example Zn, Sn and/or Be, and/or partially by a metal M(III), for example B, Fe, Co, Ni, V, Mo, Mn, As, Sb, Bi, La, Ga, In, Y, Sc and/or Cr (II=oxidation state 2, III=oxidation state 3, IV=oxidation state 4).

Said zeolites are usually prepared by reacting a mixture of an $SiO_2$ source and a metal source (for example M=Al, Zn, Be, B, Fe, Co, Ni, V, Mo, Mn, As, Sb, Bi, La, Ga, In, Y, Sc, Cr, Ti, Zr, Ge, Hf and/or Sn in the oxidation states as described above) and a nitrogen-containing base as template ("template compound"), for example tetraalkylammonium salt, if desired with addition of basic compounds (for example caustic lyes), in a pressure vessel under elevated temperature for a period of several hours or a few days, giving a crystalline product. This is separated of (for example filtered off, spray-dried or precipitated), washed, dried and, for removal of the organic nitrogen base, calcined at elevated temperature (see below). The synthesis is optionally also possible without a template if the formation of the zeolite is guaranteed. In the resultant powder, the metal (for example M=Al, Zn, Be, B, Fe, Co, Ni, V, Mo, Mn, As, Sb, Bi, La, Ga, In, Y, Sc, Cr, Ti, Zr, Ge, Hf and/or Sn in the oxidation states as described above) is at least partly present within the zeolite lattice in varying proportions with tetra-, penta- or hexa-coordination.

The zeolites used in according with the invention can be prepared by the process described and/or are commercially available.

If the zeolite catalyst to be employed in accordance with the invention, preferably of the pentasil type, is not at least partly in the preferred acidic $H^+$ form and/or $NH_4^+$ form owing to the type of production, but is, for example, in the $Na^+$ form (or any other metal-salt form desired), this can, in according with the prior art, be converted at least partly into the preferred $H^+$ and/or $NH_4^+$ form by ion exchange, for example with ammonium ions, followed by calcination (see below). The treatment with dilute protic acid, for example mineral acid, which is likewise known from the literature for conversion of the zeolite at least partly into the $H^+$ form is just as practicable. Suitable here are all protic acids, for example hydrochloric acid or sulfuric acid (see below).

It is subsequently possible to convert the zeolite catalyst exchanged in this way into the desired $Me^+$ form and contains $H^+$ and/or $NH_4^+$ by ion exchange with a corresponding metal-salt solution (metal Me=alkali metal, alkaline-earth metal or transition metal).

In order to achieve the highest possible selectivity, high conversions and particularly long catalyst service lives, it may be advantageous to modify the zeolite catalysts as claimed.

A suitable modification of the zeolite catalysts consists in, as described in 'J. Weitkamp et al., Catalysis and Zeolites, Chapter 3: Modification of Zeolites, Springer Verlag, 1999', subjecting the zeolite material—shaped or unshaped—to treatment in accordance with the known prior art (EP-A-382 055, p. 4, lines 2ff+lines 20ff; DE-C2-24 34 913, p. 3, lines 23ff; U.S. Pat. No. 5,041,548, p. 4, lines 27ff) with concentrated or dilute protic acids—for example hydrochloric acid, sulfuric acid, hydrofluoric acid, phosphoric acid, a carboxylic acid, dicarboxylic acid or polycarboxylic acid—and/or complexing agents—for example acetylacetonate (acac), nitrilotriacetic acid, sulfosalicylic acid, ethylenediaminetetraacetic acid (EDTA)—for example in accordance with EP-A-842 936 and RU-C1-21 14 849, and/or steam.

In a particular embodiment, doping of the zeolites used in the process according to the invention can be carried out by application of transition metals, sub-groups I to VIII, preferably from sub-groups I, II, IV and VIII, particularly preferably Zn, Ti, Zr, Fe, Co, Ni, Cr or V.

The application can be carried out by impregnation of the zeolite used in the process according to the invention in aqueous metal-salt solutions, by spraying corresponding metal-salt solutions onto the zeolite or by other suitable methods known from the prior art. Suitable metal salts for the preparation of the metal-salt solutions are the nitrates, nitrosylnitrates, halides, carbonates, carboxylates, acetylacetonates, chloro complexes, nitro complexes or amine complexes of the corresponding metals, the nitrates and nitrosyl nitrates being preferred. In the case of zeolites which have been doped with a plurality of metals, the metal salts or metal-salt solutions can be applied simultaneously or successively.

The zeolites coated or impregnated with the metal-salt solutions are subsequently dried, preferably at temperatures of from 60 to 150° C., and optionally calcined at temperatures of from 200 to 950° C., preferably from 400 to 750° C. In the case of separate impregnation, the catalyst is dried after each impregnation step and optionally calcined as described above. The sequence in which the transition metals are impregnated is freely selectable. The coated and dried and optionally calcined zeolites are subsequently optionally activated by treatment in a gas stream containing free hydrogen at temperatures of from 30 to approximately 600° C., preferably from 150 to approximately 450° C. The gas stream preferably consists of from 50 to 100% by volume of hydrogen and from 0 to 50% by volume of nitrogen.

The transition-metal solutions are applied to the zeolite in such an amount that the total content of transition metal, in each case based on the total weight of the catalyst, is from approximately 0.01 to approximately 10% by weight, preferably from approximately 0.01 to 5% by weight, further preferably from approximately 0.01 to approximately 2% by weight and in particular from approximately 0.05 to 1% by weight.

The transition-metal surface area on the catalyst is in total preferably from approximately 0.01 to approximately 10 $m^2/g$, further preferably from 0.05 to 5 $m^2/g$ and in particular from approximately 0.05 to 3 $m^2/g$ ($m^2$ per g of the catalyst). The metal surface area is determined by the chemisorption method described by J. LeMaitre et al. In "Characterization of Heterogeneous Catalysts", Editor Francis Delanny, Marcel Dekker, N.Y. 1984, pp. 310–324.

In order to increase the service life, the zeolites to be employed in accordance with the invention may be supported, for example on cellulose materials, clays, polymers, metals, graphites, binders or metal oxides, such as aluminas, aluminum oxide or silicon dioxide. It is furthermore possible to employ this as granules, in bead form or applied to glass or other elements, for example woven fabrics (in particular metal meshes) of any type.

Solidifying shaping processes which can be employed for the zeolites to be employed in accordance with the invention are in principle all methods for achieving corresponding shaping. Preference is given to processes in which the shaping is carried out by tableting or extrusion. Particular preference is given to processes in which the shaping is carried out by extrusion in conventional extruders, for example to give extrudates having a diameter of usually from 1 to 10 mm, in particular from 2 to 5 mm. If binders and/or auxiliaries are required, the extrusion or tableting is advantageously preceded by a mixing or compounding process. If desired, the extrusion/tableting is also followed by a calcination step. The moldings obtained are, if desired, comminuted, preferably to give granules or grit having a particular diameter of from 0.5 to 5 mm, in particular from 0.5 to 2 mm. These granules or grit and also catalyst moldings generated in another manner contain virtually no relatively fine-grained components than those having a minimum particle diameter of 0.5 mm.

In a preferred embodiment, the shaped zeolite to be employed in according with the invention comprises up to 80% by weight of binders, based on the total weight of the catalyst. Particularly preferred binder contents are from 1 to 60% by weight, in particular from 20 to 45% by weight. Suitable binders are in principle all compounds employed for purposes of this type, preferably compounds, in particular oxides, of silicon, aluminum, boron, phosphorus, zirconium and/or titanium. Of particular interest as binder is silicon dioxide, where the $SiO_2$ may also be introduced into the shaping process as silica sol or in the form of tetraalkoxysilanes. Also suitable as binders are oxides of magnesium and beryllium and clays, for example montmorillonite, kaolins, bentonites, halloysites, dickites, nacrites and anauxites.

Examples of auxiliaries which may be mentioned for the solidifying shaping processes are extrusion auxiliaries; a conventional extrusion agent is methylcellulose. Agents of this type are generally burnt completely in the subsequent calcination step.

The calcination of the zeolite catalyst to be employed in according with the invention is carried out at temperatures of from 250 to 950° C., preferably at from 400 to 750° C., particularly preferably at from 450 to 600° C., for the duration of, in general, at least one hour, preferably for 2–5 hours. The calcination is carried out in a gas atmosphere, for example nitrogen, air or noble-gas atmosphere. In general, the calcination is carried out in oxygen-containing atmospheres, with the oxygen content being from 0.1 to 90% by volume, preferably from 0.2 to 22% by volume, particularly preferably from 10 to 22% by volume. The use of other oxygen-supplying substances is likewise possible. The long-term "oxygen-supplying substances" covers all substances which are capable of releasing oxygen under the stated calcination conditions. Particular mention may be made of nitrogen oxides of the formula $N_xO_y$, where x and y are selected so as to give a neutral nitrogen oxide, $N_2O$, an $N_2O$-containing offgas stream from an adipic acid plant, $NO$, $NO_2$, ozone or a mixture of two or more thereof. On use of $CO_2$ as oxygen-supplying substance, temperatures of from 500° C. to 800° C. are preferably set during the calcination. Calcination under a steam atmosphere is likewise possible.

It has furthermore been recognized in accordance with the invention that, after use of the zeolite catalyst used in accordance with the invention, this can be regenerated, irrespective of its form, for example after a decrease in the activity and/or selectivity, by a method in which the regeneration is carried out by targeted burning-off of the coatings responsible for the deactivation. This is preferably carried out in an inert-gas atmosphere containing precisely defined amounts of oxygen-supplying substances. A regeneration method of this type is described, inter alia, in WO 98/55228 and DE-Al-19 72 39 49, the disclosure content of which is expressly incorporated herein in its full scope by way of reference. After the regeneration, the activity and/or selectivity of the catalyst is increased compared with the state immediately before the regeneration.

The zeolite catalyst to be employed in accordance with the invention and regenerated is heated to a temperature in the range from approximately 250° C. to 800° C., preferably from approximately 400° C. to 550° C. and in particular from approximately 450° C. to 500° C., either in the reaction apparatus (reactor) or in an external oven in an atmosphere containing from 0.1 to approximately 20 parts by volume of oxygen-supplying substances, particular preferably from 0.1 to approximately 20 parts by volume of oxygen. The heating is preferably carried out at a heating rate of from approximately 0.1° C./min. to approximately 20° C./min., preferably from approximately 0.3° C./min. to approximately 15° C./min. and in particular from 0.5° C./min. to 10° C./min.

During this heating phase, the catalyst is heated to a temperature at which the mostly organic coatings located thereon begin to decompose, while at the same time the temperature is regulated via the oxygen content and thus does not increase in such a way that damage to the catalyst structure occurs. The slow increase in the temperature or the holding at low temperature through adjustment of the corresponding oxygen content and the corresponding heating power is an essential step toward preventing local overheating of the catalyst in the case of high organic contents of the catalyst to be regenerated.

If the temperature of the offgas stream at the reactor outlet drops in spite of the increasing amounts of oxygen-supplying substances in the gas stream, the burning-off of the organic coatings is terminated. The duration of the treatment is generally in each case from approximately 1 to 30 hours, preferably from approximately 2 to approximately 20 hours and in particular from approximately 3 to approximately 10 hours.

During subsequent cooling of the catalyst regenerated in this way, it must be ensured that the cooling does not take place too quickly ("quenching") since otherwise the mechanical strength of the catalyst may be adversely affected.

It may be necessary to subject the catalyst, after the regeneration carried out by calcination, as described above, to rinsing with water and/or dilute acids, for example hydrochloric acid, in order, where necessary, to remove the inorganic content of the catalyst (alkali metal traces, etc.) remaining due to the contamination of the starting materials. Re-drying and/or calcination of the catalyst can subsequently be carried out.

In a further embodiment of the process according to the invention, the at least partially deactivated catalyst is, before the heating in accordance with the regeneration procedure, washed with a solvent in the reaction reactor or in an external reactor in order to remove target product still adhering. The washing here is carried out in such a way that, although the target products adhering in each case to the catalyst can be removed therefrom, the temperature and pressure are, however, not selected to be so high that the mostly organic coatings are likewise removed. The catalyst here is preferably merely rinsed with a suitable solvent. Suitable for this washing operation are thus all solvents in which the respective reaction product is readily soluble. The amount of solvent used and the duration of the washing operation are not crucial. The washing operation can be repeated a number of times and can be carried out at elevated temperature. On use of $CO_2$ as solvent, supercritical pressure is preferred, otherwise the washing operation can be carried out under atmospheric pressure or superatmospheric pressure or sub-critical pressure. When the washing operation is complete, the catalyst is generally dried. Although the drying operation is generally not crucial, the drying temperature should not greatly exceed the boiling point of the solvent used for the washing in order to avoid sudden evaporation of the solvent into the pores, in particular into the micropores, since this too may result in damage to the catalyst.

A preferred embodiment of the preparation process may consist in that the continuous process according to the invention for the synthesis of TEDA need not be interrupted during regeneration of the catalyst according to the invention in order to increase the process throughput. This can be achieved by the use of at least two reactors connected in parallel, which can be operated alternately.

The catalyst regeneration can be carried out in such a way that at least one of the reactors connected in parallel is decoupled from the respective reaction step, and the catalyst present in this reactor is regenerated, where at least one reactor is always available for the reaction of EDA in each step during the continuous process.

The TEDA obtained in accordance with the invention can be recrystallized from suitable solvents (for example pentane or hexane) in order to improve its purity. However, this is usually unnecessary since TEDA can be prepared by the process according to the invention with purities of greater than 95% by weight, for example greater than 97% by weight.

In a particular embodiment, the TEDA preparation process as claimed is combined with the subsequent TEDA process according to the earlier EP application No 00114475.7 of Jul. 6, 2000 (BASF AG).

In accordance with this combination, firstly TEDA is prepared as claimed. In the subsequent work-up of the TEDA (for example by distillation), which may be multistep, the TEDA is evaporated, preferably in the final work-up step (in particular distillation or rectification step), and the vapor-form TEDA obtained, for example, at the top or in a side take-off of the distillation column, which preferably has a purity of greater than 95% by weight, in particular greater than 97% by weight, is introduced into a liquid solvent. This introduction of the vapor-form TEDA directly into a liquid solvent is also referred to below as TEDA quenching.

By subsequent crystallization of the TEDA out of the resultant solution, pure TEDA of high quality is obtained.

The liquid solvent is generally selected from the group consisting of cyclic or acyclic hydrocarbons, chlorinated aliphatic hydrocarbons, aromatic hydrocarbons, alcohols, ketones, aliphatic carboxylic esters, aliphatic nitriles and ethers.

For the preparation of a solution of pure TEDA in accordance with the above process combination which can be used, for example, as catalyst solution in the production of polyurethane foam, the solvent employed for the TEDA quenching is preferably an alcohol (for example ethylene glycol, 1,4-butanediol or preferably dipropylene glycol). The color number of a 33% strength by weight TEDA solution in dipropylene glycol obtained in this way is less than 150 APHA, in particular less than 100 APHA, very particularly less than 50 APHA.

For the preparation of pure (crystalline) TEDA in accordance with the above process combination, the solvent used for the TEDA quenching is preferably an aliphatic hydrocarbon, in particular a saturated aliphatic hydrocarbon having 5 to 8 carbon atoms (for example hexane, heptane or preferably pentane). The crystallization of the pure TEDA from the TEDA solution prepared in accordance with the invention can be carried out by methods known to the person skilled in the art. The TEDA crystals obtained by subsequent multistep, or preferably single-step, crystallization are of high purity (purity of, in general, at least 99.5% by weight, in particular at least 99.8% by weight, content of PIP less than 0.1% by weight, in particular less than 0.05% by weight, content of N-ethylpiperazine less than 0.02% by weight, in particular less than 0.01% by weight), and the color number of a 33% strength by weight solution in dipropylene glycol is less than 50 APHA, in particular less than 30 APHA.

(All APHA numbers in accordance with ISO 6271).

The introduction of the vapor-form TEDA into the liquid solvent is carried out in a quenching apparatus, for example preferably in a falling-film condenser (thin-film, trickle-film or falling-flow condenser) or in a jet apparatus. The vapor-form TEDA here can be transported in cocurrent or in countercurrent with the liquid solvent. It is advantageous to introduce the vapor-form TEDA into the quenching apparatus from the top. It is furthermore advantageous to feed the liquid solvent in tangentially at the top of the falling-film condenser or to feed the liquid solvent through one or more nozzles in order to achieve complete wetting of the interior wall of the quenching apparatus.

In general, the temperature in the TEDA quenching is set by controlling the temperature of the solvent employed and/or of the quenching apparatus to from 20 to 100°0 C., preferably from 30 to 60° C. The absolute pressure in the TEDA quenching is generally from 0.5 to 1.5 bar.

In general, depending on the type of solvent, firstly solutions having a TEDA content of from about 1 to 50% by weight, preferably from 20 to 40% by weight, are obtained during the TEDA quenching.

EXAMPLES

Catalyst A:

Firstly, a TS-1 zeolite powder (pentasil, MFI structure) was prepared as described in Example 1 of DE-A-196 23

611 (SiO$_2$/TiO$_2$ ≈40 [mol/mol]). Before the extrusion with 20% by weight of SiO$_2$ (based on the total weight of the finished extrudates), the zeolite powder was treated with 5 M HCl, washed a number of times with water and calcined at 500° C. for 5 hours. The 2 mm extrudates were subsequently calcined at 500° C. for 5 hours.

EXAMPLE 1

Continuous preparation of TEDA

The catalyst shown in the table below was employed in a gas-phase apparatus (heated tubular reactor: length: 1000 mm, diameter 6 mm). Starting-material mixture: 35% of EDA, 15% of PIP, 50.0% of water (all data in % by weight). The aqueous starting-material mixture was pumped directly into the reactor and evaporated in the upper part at a reaction temperature of 345° C. before being passed onto the catalyst without pressure. Weight hourly space velocity: 1.0 kg of starting-material mixture/kg of catalyst*h. The reaction products were condensed at the reactor outlet in a condenser and collected, and an aliquot was analyzed by gas chromatography.

GC analysis:
Column: RTX-5, 30 m; temperature program: 80° C.-5° C./min.-280° C., detector: FID, internal standard: N-methylpyrrolidone (NMP).

Evaluation:

TABLE 1

Synthesis of triethylenediamine (TEDA) from ethylenediamine (EDA) and piperazine (PIP); feed: 35:15:50 EDA:PIP:H$_2$O in % by weight; modulus: SiO$_2$/TiO$_2$ molar ratio of the zeolites used.

| Example | Catalyst | Modulus [SiO$_2$/M$_x$O$_{x+1}$] | U$_{EDA}$ [%] | U$_{PIP}$ [%] | S$_{TEDA}$ [%] |
|---|---|---|---|---|---|
| 1 | A | 40 (M = Ti, x = 1) | >95 | 11 | 95 |

(U = conversion in % by weight based on the employed amount of substance given in the table (EDA or PIP);
S = Selectivity, based on reacted —CH$_2$—CH$_2$— units originating from EDA and PIP).

We claim:

1. A process for the preparation of triethylenediamine (TEDA), which comprises reacting ethylenediamine (EDA) and one or more amine compounds selected from the group consisting of monoethanolamine, diethanolamine, triethanolamine, piperazine (PIP), diethylenetriamine, triethylenetetramine, tri(2-aminoethyl)amine, N-(2-aminoethyl)ethanolamine, N-(2-hydroxyethyl)piperazine and N-(2-aminoethyl)piperazine, in the presence of a zeolite catalyst, wherein the zeolite catalyst comprises one or more metals M in oxidation state III or IV as oxides, and for M=Al, has an SiO$_2$/M$_2$O$_3$ molar ratio of greater than 1400:1 to 40,000:1, for M=metal in oxidation state III or M=two or more metals in oxidation state III, has an SiO$_2$/M$_2$O$_3$ molar ratio of from greater than 100:1 to 40,000:1, and for M=metal in oxidation state IV or M=two or more metals in oxidation state IV, has an SiO$_2$ /M$_2$ molar ratio of from greater than 100:1 to 40,000:1, and the reaction temperature is from 250 to 500° C.

2. A process as claimed in claim 1, wherein the reaction is carried out continuously.

3. A process as claimed in claim 1, wherein the reaction is carried out in the gas phase.

4. A process as claimed in claim 1, wherein the reaction is carried out in the presence of a solvent or diluent.

5. A process as claimed in claim 1, wherein the reaction is carried out in the presence of water or ammonia.

6. A process as claimed in claim 1, wherein the reaction is carried out in the presence of from 2 to 1200% by weight of water, based on EDA employed.

7. A process as claimed in claim 1, wherein the reaction is carried out in the presence of from 14 to 300% by weight of water, based on EDA employed.

8. A process as claimed in claim 1, wherein EDA and from 1 to 1000% by weight of piperazine (PIP), based on EDA, are reacted.

9. A process as claimed in claim 1, wherein EDA and from 7 to 250% by weight of piperazine (PIP), based on EDA, are reacted.

10. A process as claimed in claim 1, wherein EDA, from 8 to 250% by weight of PIP and from 23 to 300% by weight of water, in each case based on EDA, are reacted.

11. A process as claimed in claim 1, wherein PIP arising after the reaction is separated off and fed back into the reaction with EDA.

12. A process as claimed in claim 1, wherein the consumption of PIP in the overall balance is from 0 to 30 kg per 100 kg of TEDA.

13. A process as claimed in claim 1, wherein the reaction temperature is from 310 to 390° C.

14. A process as claimed in claim 1, wherein the absolute pressure is from 0.1 to 10 bar.

15. A process as claimed in claim 1, wherein the WHSV (weight hourly space velocity), based on the amines employed in the reaction, is from 0.05 to 6h$^{-1}$.

16. A process as claimed in claim 1, wherein the zeolite catalyst, for M=Al, has an SiO$_2$ /M$_2$O$_3$ molar ratio of from greater than 1400 to 40,000:1.

17. A process as claimed in claim 1, wherein the zeolite catalyst, for M=metal in oxidation state III or M=two or more metals in oxidation state III, has an SiO$_2$/M$_2$O$_3$ molar ratio of from greater than 100:1 to 5,000:1.

18. A process as claimed in claim 1, wherein the zeolite catalyst, for M=metal in oxidation state IV or M=two or more metals in oxidation state IV, has an SiO$_2$/MO$_2$ molar ratio of from greater than 10:1 to 5,000:1.

19. A process as claimed in claim 1, wherein the zeolite catalyst is a pentasil zeolite.

20. A process as claimed in claim 1, wherein the metal M in oxidation state III is selected from the group consisting of Al, B, Fe, Co, Ni, V, Mo, Mn, As, Sb, Bi, La, Ga, In, Y, Sc and Cr, and mixtures thereof.

21. A process as claimed in claim 1, wherein the metal M in oxidation state IV is selected from the group consisting of Ti, Zr, Ge, Hf and Sn, and mixtures thereof.

22. A process as claimed in claim 1, wherein the zeolite catalyst is of the MFI or MEL structural type or mixed structures thereof (MEL/MFI or MFI/MEL).

23. A process as claimed in claim 1, wherein the zeolite catalyst exists or is employed at least partly in the H$^+$ and/or NH$_4$$^+$ form under the reaction conditions if Al and/or other metals M are in oxidation state III in the zeolite.

24. A process as claimed in claim 1, wherein the zeolite catalyst is treated with a protic acid before use in the process.

25. A process as claimed in claim 1, wherein the zeolite catalyst has been doped with one or more transition metal selected from sub-groups I to VIII of the Periodic Table of the Elements.

26. A process as claimed in claim 1, wherein the zeolite catalyst comprises silicon dioxide as binder.

27. A process as claimed in claim 1, wherein a zeolite catalyst which has been treated or regenerated in a gas atmosphere in the presence of oxygen or oxygen-supplying substances at a temperature in the range from 250 to 800° C. is employed at least partly.

28. A process as claimed in claim 1, wherein the process is carried out without interruption in at least two reactors connected in parallel, of which in each case one can be decoupled from the starting-material and product stream for regeneration of the zeolite catalyst.

29. A process for the preparation of a solution of TEDA, which comprises preparing TEDA as claimed in claim 1, evaporating the prepared TEDA, and passing the vapor-form TEDA into a liquid solvent.

30. A process for the preparation of TEDA, which comprises preparing a solution of pure TEDA as claimed in claim 26, and subsequently crystallizing the TEDA out of this solution.

31. A process as claimed in claim 29, wherein the liquid solvent is selected from the group consisting of cyclic and acyclic hydrocarbons, chlorinated aliphatic hydrocarbons, aromatic hydrocarbons, alcohols, ketones, aliphatic carboxylic esters, aliphatic nitrites and ethers.

* * * * *

UNITED STATES PATENT AND TRADEMARK OFFICE
CERTIFICATE OF CORRECTION

PATENT NO.     : 6,562,971 B2
DATED          : May 13, 2003
INVENTOR(S)    : Frauenkron et al.

It is certified that error appears in the above-identified patent and that said Letters Patent is hereby corrected as shown below:

Column 15,
Line 55, "of greater" should be -- of from greater --;
Line 61, "/M$_2$" should be -- MO$_2$ --;
Line 62, "100:1" should be -- 10:1 --.

Column 16,
Line 35, "40,000:1" should be -- 5,000:1 --;
Line 54, "the MFI or MEL structural type" should be -- an MFI or MEL structure --;
Line 63, "metal" should be -- metals --.

Signed and Sealed this

Sixteenth Day of September, 2003

JAMES E. ROGAN
*Director of the United States Patent and Trademark Office*

UNITED STATES PATENT AND TRADEMARK OFFICE
CERTIFICATE OF CORRECTION

PATENT NO.    : 6,562,971 B2
DATED         : May 13, 2003
INVENTOR(S)   : Frauenkron et al.

It is certified that error appears in the above-identified patent and that said Letters Patent is hereby corrected as shown below:

<u>Column 18,</u>
Line 5, "26" should be -- 29 --;
Line 7, "and" should be -- or --.

Signed and Sealed this

Twenty-fourth Day of February, 2004

JON W. DUDAS
*Acting Director of the United States Patent and Trademark Office*